US012767921B2

United States Patent

(12) Ban et al.

(10) Patent No.: US 12,767,921 B2
(45) Date of Patent: Oct. 20, 2026

(54) CELL PRODUCTION DEVICE AND CELL PRODUCTION METHOD

(71) Applicants: FANUC CORPORATION, Yamanashi (JP); I Peace, Inc., Palo Alto, CA (US)

(72) Inventors: Kazunori Ban, Yamanashi (JP); Satoshi Kinoshita, Yamanashi (JP); Koji Tanabe, Palo Alto, CA (US); Ryoji Hiraide, Kyoto (JP)

(73) Assignees: FANUC CORPORATION, Yamanashi (JP); I PEACE, INC., Palo Alto, CA (US)

( * ) Notice: Subject to any disclaimer, the term of this patent is extended or adjusted under 35 U.S.C. 154(b) by 1058 days.

(21) Appl. No.: 17/637,812

(22) PCT Filed: May 28, 2020

(86) PCT No.: PCT/JP2020/021240
§ 371 (c)(1),
(2) Date: Feb. 24, 2022

(87) PCT Pub. No.: WO2021/038996
PCT Pub. Date: Mar. 4, 2021

(65) Prior Publication Data

US 2023/0038829 A1 Feb. 9, 2023

Related U.S. Application Data

(60) Provisional application No. 62/893,605, filed on Aug. 29, 2019.

(51) Int. Cl.
*C12M 1/36* (2006.01)
*C12M 1/00* (2006.01)
(Continued)

(52) U.S. Cl.
CPC ............ *C12M 41/48* (2013.01); *C12M 23/04* (2013.01); *C12M 23/14* (2013.01); *C12M 23/22* (2013.01);
(Continued)

(58) Field of Classification Search
None
See application file for complete search history.

(56) References Cited

U.S. PATENT DOCUMENTS 6,645,432 B1 11/2003 Anderson et al.
10,227,554 B2 3/2019 Janas
(Continued)

FOREIGN PATENT DOCUMENTS

CN 103667054 A 3/2014
JP H9500818 A 1/1997
(Continued)

OTHER PUBLICATIONS

Document entitled WO2006043642A1 Fluid Reactor, machine translation of WO 2006/043642 A1 provided by Espacenet, original document published 2006. (Year: 2006).*

*Primary Examiner* — Michael A Marcheschi
*Assistant Examiner* — Ashley Lopezlira
(74) *Attorney, Agent, or Firm* — HAUPTMAN HAM, LLP

(57) ABSTRACT

This cell production device comprises: a cell production plate that includes a fluid circuit in which a plurality of functional sites are integrated; and a closed type connector that connects the fluid circuit to an external space in a closed manner, wherein the fluid circuit comprises, as the plurality of functional sites, an injection and discharge unit that injects or discharges a fluid into or out of the fluid circuit via the closed type connector, a variable volume unit that stores a fluid that is extruded or withdrawn by the injected or
(Continued)

discharged fluid, and a cell induction and culture unit that performs at least one of induction and culture of cells based on the injected fluid.

17 Claims, 9 Drawing Sheets

(51) Int. Cl.
*C12M 1/06* (2006.01)
*C12M 1/12* (2006.01)
*C12M 1/26* (2006.01)
*C12M 1/34* (2006.01)

(52) U.S. Cl.
CPC ............ *C12M 23/34* (2013.01); *C12M 23/38* (2013.01); *C12M 25/06* (2013.01); *C12M 27/02* (2013.01); *C12M 29/00* (2013.01); *C12M 33/04* (2013.01); *C12M 41/00* (2013.01); *C12M 47/04* (2013.01)

(56) References Cited

U.S. PATENT DOCUMENTS

| | | | | |
|---|---|---|---|---|
| 2009/0014360 | A1* | 1/2009 | Toner | C12M 23/16 209/208 |
| 2013/0171628 | A1* | 7/2013 | Di Carlo | C12M 29/00 435/7.1 |
| 2014/0087413 | A1* | 3/2014 | Newbold | G01N 1/14 435/29 |
| 2014/0193895 | A1 | 7/2014 | Smith et al. | |
| 2015/0231634 | A1* | 8/2015 | Szita | C12M 29/10 435/395 |
| 2017/0283761 | A1* | 10/2017 | Corso | C12M 35/02 |
| 2017/0307502 | A1* | 10/2017 | Mason | B01J 19/0046 |
| 2019/0185805 | A1* | 6/2019 | Kohoutek | C12M 25/06 |
| 2020/0269234 | A1* | 8/2020 | Kujala | C12M 23/16 |

FOREIGN PATENT DOCUMENTS

| | | | |
|---|---|---|---|
| JP | 2002512783 | A | 5/2002 |
| JP | 200580607 | A | 3/2005 |
| JP | 2005287425 | A | 10/2005 |
| JP | 2007136322 | A | 6/2007 |
| JP | 4183742 | B1 | 11/2008 |
| JP | 201464475 | A | 4/2014 |
| JP | 2014514926 | A | 6/2014 |
| JP | 2014226623 | A | 12/2014 |
| JP | 201746592 | A | 3/2017 |
| JP | 2017513483 | A | 6/2017 |
| JP | 2017221166 | A | 12/2017 |
| JP | 201819685 | A | 2/2018 |
| JP | 2018513684 | A | 5/2018 |
| WO | 2005049196 | A1 | 6/2005 |
| WO | 2006043642 | A1 | 4/2006 |
| WO | 2007052716 | A1 | 5/2007 |
| WO | 2012020458 | A1 | 2/2012 |
| WO | 2013175580 | A1 | 11/2013 |
| WO | 2014049701 | A1 | 4/2014 |
| WO | 2017038887 | A1 | 3/2017 |
| WO | 2017154880 | A1 | 9/2017 |
| WO | 2018154788 | A1 | 8/2018 |
| WO | 2019043130 | A1 | 3/2019 |
| WO | 2020040118 | A1 | 2/2020 |
| WO | 2020040135 | A1 | 2/2020 |

* cited by examiner

CELL PRODUCTION DEVICE AND CELL PRODUCTION METHOD

RELATED APPLICATIONS

The present application is a National Phase of International Application No. PCT/JP2020/021240, filed May 28, 2020, which claims priority to U.S. Provisional Application No. 62/893,605 filed Aug. 29, 2019.

FIELD

The present invention relates to a cell production device and a method for producing the same, and particularly to a cell production device that realizes streamlining of production of the device and compatibility of the device with automated systems at the same time and a method for producing the same.

BACKGROUND

Embryonic stem cells (ES cells) are stem cells established from early embryos of human or mouse, and they have the pluripotency to differentiate into all cells present in the body. Human ES cells are considered to be applicable for cell transplantation for many diseases such as Parkinson's disease, juvenile diabetes, and leukemia. However, ES cell transplantation, like organ transplantation, has a problem of inducing rejection. From an ethical standpoint, there are many objections to the utilization of ES cells, which are established by destroying human embryos.

To address this issue, Professor Shinya Yamanaka of Kyoto University succeeded in establishing induced pluripotent stem cells (iPS cells) by introducing four genes: Oct3/4, Klf4, c-Myc, and Sox2 into somatic cells, and was awarded the 2012 Nobel Prize in Physiology or Medicine (see, for example, Patent literature 1). iPS cells are ideal pluripotent cells with no rejection or ethical issues, and are expected to be utilized in cell transplantation methods.

Induced stem cells, such as iPS cells, are established by introducing an inducing factor, such as a gene, into the cells, which are expansively cultured and cryopreserved. However, for preparing iPS cells for clinical use (GLP, GMP grade) or the like, for example, a clean room that is kept very clean is required, which involves high maintenance costs. For industrialization, how to improve the efficiency of clean room operation methods to reduce costs has been a problem.

Although preparation of iPS cells is mostly performed manually, few technicians are capable of producing iPS cells for clinical use. The series of operations from establishment to storage of stem cells are complicated, which is a problem. Cell culture for clinical use requires three steps: confirmation of standard of process (SOP), manipulation according to SOP, and confirmation whether or not the manipulation was performed according to SOP, and it is very unproductive for a person to perform these steps. Cell culture needs to be managed 24 hours a day, every day, and stem cells can be stored for decades, which is beyond the capacity of human resources alone to manage.

Therefore, closed system cell production devices that do not require a highly clean room and can be operated in a normally controlled area (for example, grade D level or higher for at least one of microorganisms and particulates in WHO-GMP standards) have been developed (see, for example, Patent literature 2). In order to automate complex cell production processes by also eliminating human resources, cell production systems equipped with robots to assist in cell production have also been developed. The following documents are known as prior art concerning such cell production devices.

Patent literature 3 discloses a somatic cell production system that packages a pre-introduction cell delivery channel, a factor introduction device that prepares inducing factor-introduced cells by introducing somatic cell inducing factors into pre-introduction cells, and a cell production device that prepares somatic cells by culturing inducing factor-introduced cells in a single housing.

Patent literature 4 discloses a cell culture container with a closed system of culture containers and flow paths, in which the growth state of the cell culture can be clearly observed because the cell culture container holds the second container eccentrically inside the first container.

Patent literature 5 discloses a cell culture device in which a culture medium storing means, a cell inoculation means, and a culture container are configured in a closed system. The cell culture device determines the culture status of cells based on images of cells in the culture container, and performs culture operations based on this determination, which saves the operator's labor.

Patent literature 6 discloses a cell culture device comprising a main body with side walls enclosing the volume of a cell culture chamber, a lid covering the cell culture chamber, and a bottom plate arranged at the bottom of the main body, wherein microfluidic conduits are integrally formed on the main body to provide fluid communication between inlet and outlet connectors and the cell culture chamber.

Patent literature 7 discloses a microchip reaction device comprising a bubble removal means that moves bubbles in the internal space of the microchip to the external space. Patent literature 8 discloses a cell culture device with air vents that allow gas to be discharged from a first culture solution storage chamber and a second culture solution storage chamber, wherein the vents are equipped with air filters.

Patent literature 9 discloses a cell culture plate comprising a liquid mixing unit in which two flow paths merge. Patent literature 10 discloses a device comprising a substrate supporting radially distributed microchannel components and a cover plate arranged on the substrate for cell growth and cell testing. The microchannel components comprise an introduction channel for introducing a liquid sample, cell growth chambers and testing chambers with a relatively large flow area, and a discharge channel for removing the liquid sample.

Patent literature 11 discloses a culture device comprising a first layer defining a first microfluidic channel and a second layer defining a second microfluidic channel.

Patent literature 12 discloses a cell culture device comprising a flow path integrated plate and a base plate. The flow path integrated plate includes a flow path plate in which a flow path for a culture solution is formed, and a pump unit in which a group of peristaltic pumps are arranged to supply and discharge the culture solution, and the base plate includes a drive source such as a motor.

CITATION LIST

Patent literature 1: Japanese Patent 4183742
Patent literature 2: Japanese Unexamined Patent Publication No. 2018-019685
Patent literature 3: WO 2018/154788
Patent literature 4: WO 2014/049701
Patent literature 5: WO 2007/052716

Patent literature 6: Japanese Unexamined Patent Application Publication (Translation of PCT Application) No. 2014-514926

Patent literature 7: Japanese Unexamined Patent Publication No. 2014-226623

Patent literature 8: WO 2017/154880

Patent literature 9: Japanese Unexamined Patent Publication No. 2005-80607

Patent literature 10: Japanese Unexamined Patent Application Publication (Translation of PCT Application) No. 2002-512783

Patent literature 11: Japanese Unexamined Patent Application Publication (Translation of PCT Application) No. 2017-513483

Patent literature 12: Japanese Unexamined Patent Publication No. 2017-221166

SUMMARY

Technical Problem

Most of conventional cell culture devices integrate only cell culture functions, such as culture medium storing reservoirs, culture medium supply and discharge flow paths, and cell culture containers, but few integrate also cell induction functions, such as cell initiation, reprogramming, fate diversion, direct reprogramming, differentiation diversion, differentiation induction, and transformation by introducing an inducing factor. In order to configure these various functional sites in a closed system, a complicated process of connecting separate components via tubes, pumps, connectors, and the like in a closed manner is needed, which may increase the number of production man-hours and production cost. When cell production using such a device is fully automated, a cell production device composed of separate components is difficult for robots to handle.

Therefore, there is a need for a technique that realizes streamlining of production and compatibility with automated systems for cell production devices at the same time.

Solution to Problem

One aspect of the present disclosure provides a cell production device comprising: a cell production plate comprising a fluid circuit in which a plurality of functional sites are integrated; and a closed type connector that connects the fluid circuit to an external space in a closed manner, wherein the fluid circuit comprises, as a plurality of functional sites, an injection and discharge unit that injects or discharges a fluid into or out of the fluid circuit via a closed type connector, a variable volume unit that stores a fluid that is extruded or withdrawn by the injected or discharged fluid, and a cell induction and culture unit that performs at least one of induction and culture of cells based on the injected fluid.

Another aspect of the present disclosure provides a method for producing a cell production device comprising: a process of forming a flat plate that includes a fluid circuit in which a plurality of functional sites are integrated; a process of forming a cell production plate by fixing a lid to the flat plate in such a manner to cover the fluid circuit; and a process of attaching a closed type connector to the cell production plate to connect the fluid circuit to an external space in a closed manner, wherein the fluid circuit comprises, as a plurality of functional sites, at least one of the following: an injection and discharge unit that injects or discharges a fluid into or out of the fluid circuit via a closed type connector; a variable volume unit that stores a fluid that is extruded or withdrawn by the injected or discharged fluid; a transfer unit that transfers the injected fluid in the fluid circuit; and a cell induction and culture unit that performs at least one of induction and culture of cells based on the injected fluid.

Another aspect of the present disclosure provides a cell production device comprising: a cell production plate that includes a fluid circuit in which a plurality of functional sites are integrated; and a closed type connector that connects the fluid circuit to an external space in a closed manner, wherein the fluid circuit comprises, as a plurality of functional sites, an injection and discharge unit that injects or discharges a fluid into or out of the fluid circuit via a closed connector, and a cell induction and culture unit that performs at least one of induction and culture of cells based on the injected fluid.

Advantageous Effects of Invention

According to the present disclosure, since a plurality of functional sites are integrated in one cell production plate, production processes such as the closed connection of separate components via tubes, pumps, connectors, and the like are unnecessary, thereby reducing the production man-hours, production costs, and the like of cell production devices. At the same time, the fluid that is extruded or withdrawn by the injected or discharged fluid is confined within the fluid circuit, which eliminates the need to escape the fluid outside the cell production plate or to take in fluid from the outside, and therefore it is possible to form the cell production plate into a plate shape while maintaining the sealability of the fluid circuit. Such a cell production plate is easy for a robot to handle and improves the compatibility with automated systems.

DESCRIPTION OF EMBODIMENTS

Embodiments of the present disclosure will be described in detail with reference to the accompanying drawings. In each drawing, the same or similar symbols are assigned to the same or similar components. The embodiments described below are not intended to limit the technical scope of the invention and the meaning of the terms in claims. The term "closed" in this document means that sources of contamination, such as microorganisms or viruses, do not enter the device and cause biological contamination, and/or that fluids (including substances such as cells, microorganisms, viral particles, proteins, and nucleic acids) inside the device do not leak and cause cross-contamination, and/or that handling donor fluids infected with pathogens inside the device do not create a biohazard. Note, however, that the device herein may be configured to allow fluids that are not sources of contamination, such as carbon dioxide, nitrogen, or oxygen, to enter or leak outside the device.

Figure 1:
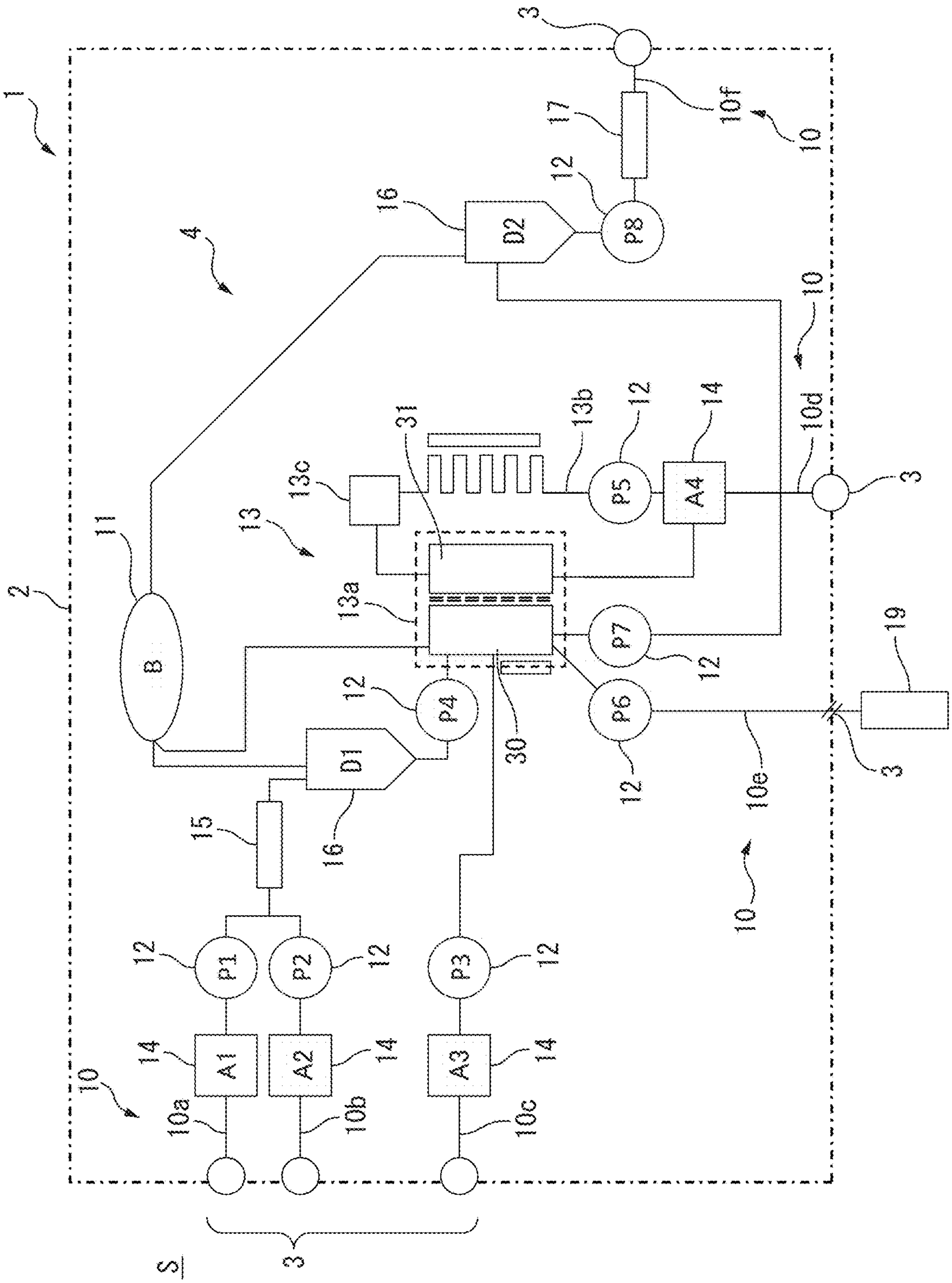
FIG. 1 is a configuration diagram of a cell production device in one embodiment.

FIG. 1 illustrates the configuration of a cell production device 1 in the present embodiment. The cell production device 1 is a cell induction device with a cell induction function that performs cell initialization, reprogramming, fate diversion, direct reprogramming, differentiation diversion, differentiation induction, transformation, or the like by introducing an inducing factor, or may be a cell culture device that only has a cell culture function merely performing culture, expansion culture, or the like. The cell production device 1 injects a fluid containing source cells (for example, somatic cells such as blood cells or fibroblasts, or stem cells such as ES cells or iPS cells), produces target cells (for example, stem cells, progenitor cells, or final differentiated cells) from the source cells, and discharges the fluid containing the target cells. As the target cells, differentiated cells such as fibroblasts, neural cells, retinal epithelial cells, hepatocytes, β cells, renal cells, mesenchymal stem cells, blood cells, megakaryocytes, T cells, chondrocytes, cardiomyocytes, myocytes, vascular cells, epithelial cells, renal cells, or other somatic cells may be prepared. The cell production device 1 is a closed system cell processing device that integrates all parts that should be highly clean inside, and can be used in normally controlled areas. The closed space inside the device is configured in such a manner that gases, viruses, microorganisms, impurities, or the like are not exchanged with the outside. Note, however, that the device may be configured to allow exchange of non-contaminant fluids between the inside and outside of the device by additionally providing the device with a fluid exchange filter, or the like, as described below.

As illustrated in FIG. 1, the cell production device 1 includes a cell production plate 2 and a closed type connector 3. The cell production plate 2 includes a fluid circuit 4 in a closed system that is shut off from an external space S, and the fluid circuit 4 includes a flow path that highly integrates a plurality of functional sites. The closed type connector 3 is a connector for injecting a fluid into the fluid circuit 4 or for discharging a fluid from the fluid circuit 4, and is attached to the cell production plate 2. The closed type connector 3 is a connector that connects the fluid circuit 4 and a fluid container to the external space S in a closed manner, and may be, for example, a sterile connection connector, a needleless connector, a needle connector, or a heat-fused tube. The needleless connector may be a split septum type or a mechanical valve type. The fluid container is a syringe, variable volume bag, or the like, and when the closed type connector 3 is connected to the fluid container, the fluid circuit 4 is in fluid communication with the fluid container, while when the closed type connector 3 is not connected to the fluid container, the fluid circuit 4 is shut off from the external space S. This prevents biological contamination, cross-contamination, and biohazard of the fluid circuit 4. In order to enable injection or discharge of a plurality of types of fluids, the cell production device 1 preferably includes a plurality of closed type connectors 3.

Figure 2:
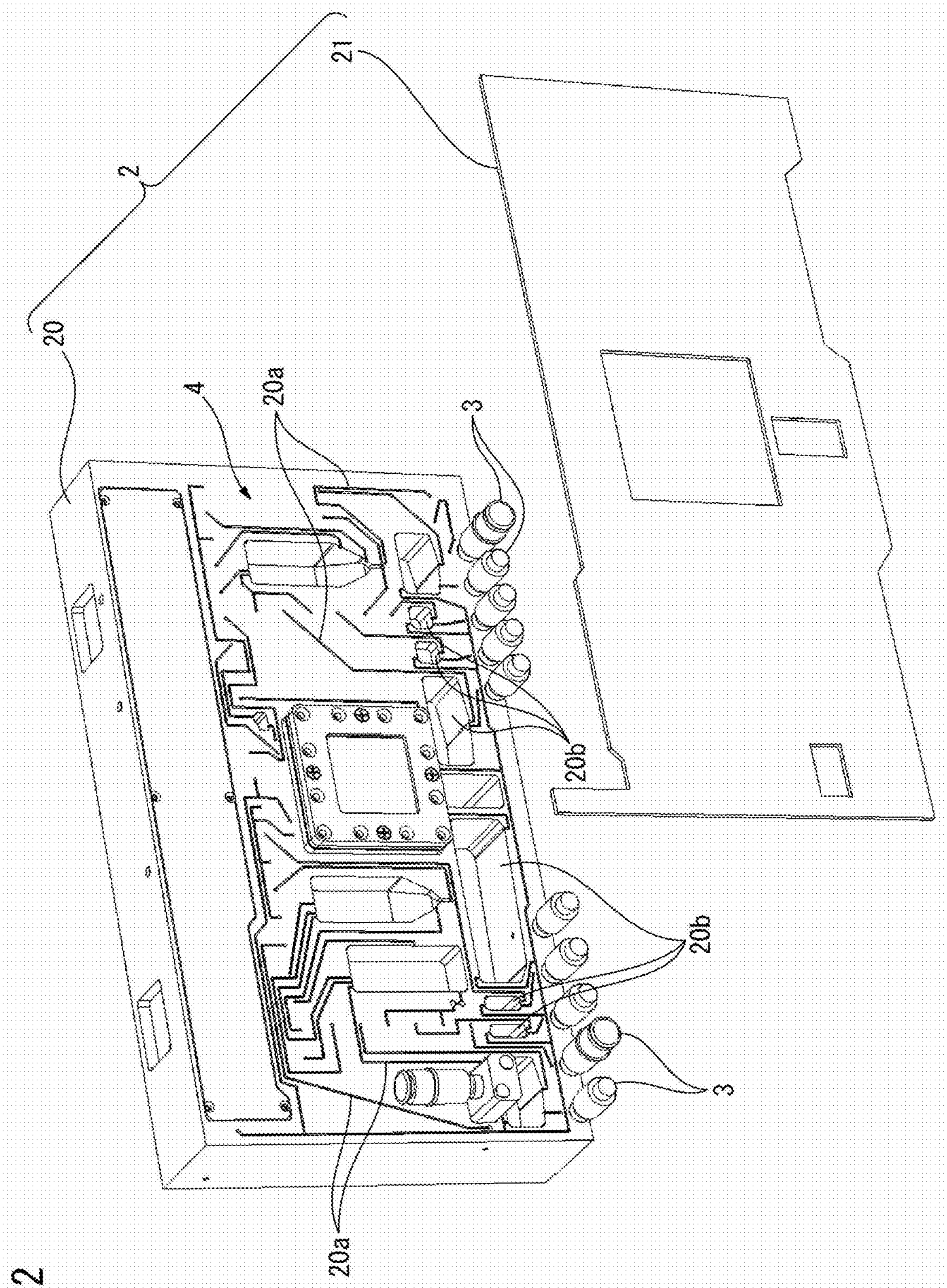
FIG. 2 is an exploded perspective view of one example of a cell production plate.

FIG. 2 illustrates one example of a cell production plate 2. As illustrated in FIG. 2, the cell production plate 2 includes a flat plate 20 and a lid 21. The flat plate 20 can be molded from, for example, a biologically safe resin or metal. The flat plate 20 is preferably molded by a molding process using a mold, such as injection molding or compression molding, and the flat plate 20 may also be molded using a 3D printer or the like. A 3D printer can employ a variety of molding methods, such as optical molding, thermal dissolution layering, powder sintering, or inkjet. On at least one of the surface and the back of the flat plate 20, a groove 20*a* is provided as a flow path for fluid flow, and a plurality of grooves 20*a* are combined to form the fluid circuit 4. A portion of the fluid circuit 4 is provided with a groove 20*a* that is relatively larger in width or depth to form a reservoir tank 20*b* for temporary storage of fluid. Walls of the groove 20*a* and reservoir tank 20*b* may be coated with poly-HEMA (poly 2-hydroxyethyl methacrylate) to make the walls non-adhesive to cells. Conversely, when cells have difficulty entering the groove 20*a* or reservoir tank 20*b*, walls of the groove 20*a* and reservoir tank 20*b* may be made low protein adsorbent. At least a portion of the grooves 20*a* and reservoir tanks 20*b* are preferably white or black in order to observe changes over time in fluid, cells, cell masses, or the like by image recognition sensors, ultrasonic recognition sensors, or the like.

The lid 21 may be made of, for example, a biologically safe resin, quartz glass, or the like. The lid 21 (or at least a portion of the cell production plate 2) is preferably transparent in order to observe changes over time of fluid, cells, cell masses, or the like in the fluid circuit 4 by image recognition sensors, ultrasonic recognition sensors, or the like. This observation enables transition to the next cell production process when appropriate. The lid 21 is fixed to the flat plate 20 in such a manner that the lid covers the fluid circuit 4 by a biologically safe fixing method, such as chemical bonding, weld bonding, or adhesive bonding, in order to shut off the fluid circuit 4 from the external space. For chemical bonding, silane coupling agents, plasma irradiation, or the like may be used. For weld bonding, laser welding, ultrasonic welding, or the like may be used, and for adhesive bonding, UV-curing adhesives or the like may be used. After fixing the flat plate 20 and the lid 21, the cell production plate 2 is subjected to sterilization, such as heat sterilization, gamma ray sterilization, UV sterilization, or electron beam sterilization, to make the fluid circuit 4 highly clean.

Figure 3A:
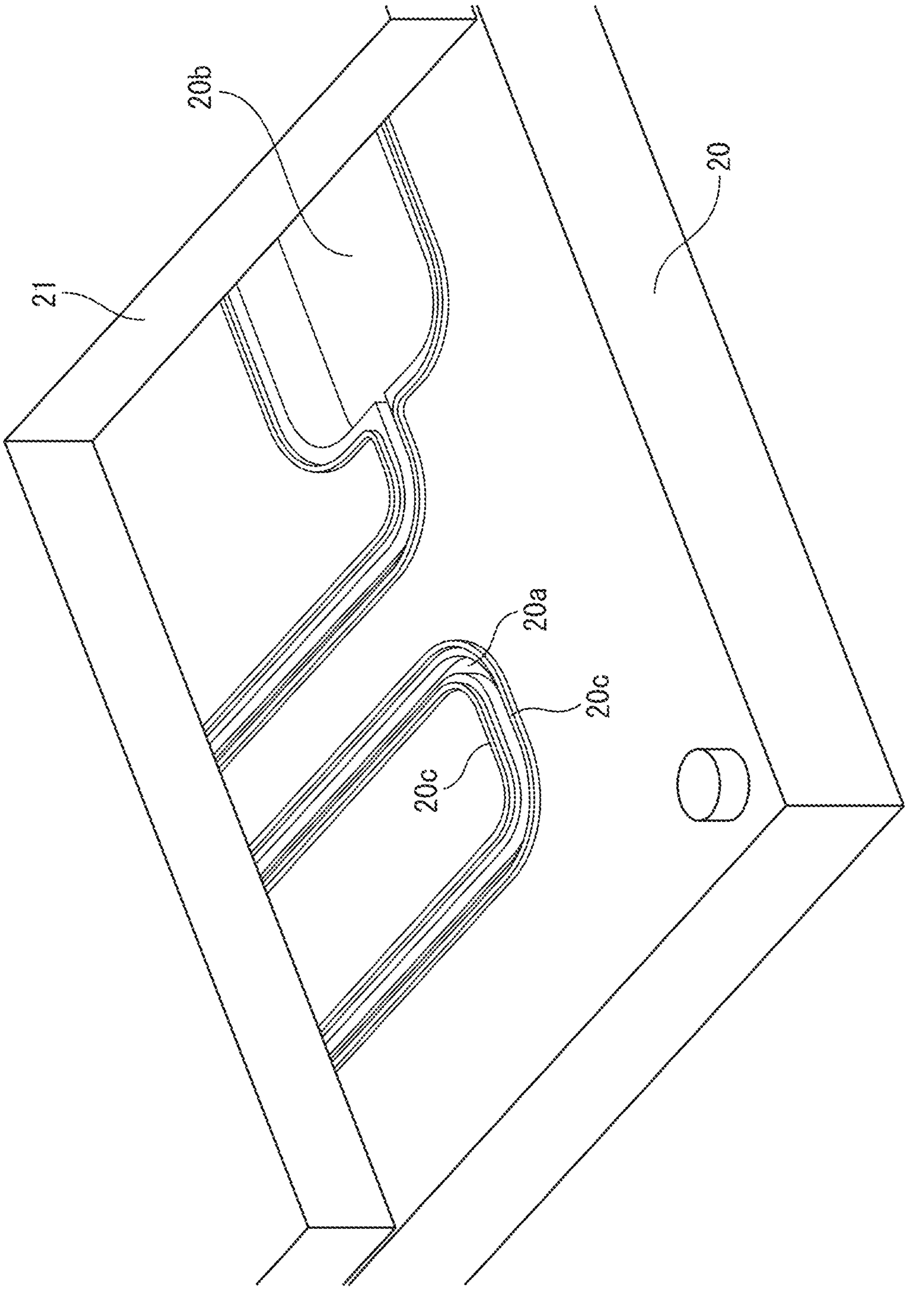
FIG. 3A is an enlarged sectional view of one example of a method of fixing a flat plate and a lid.
Figure 3B:
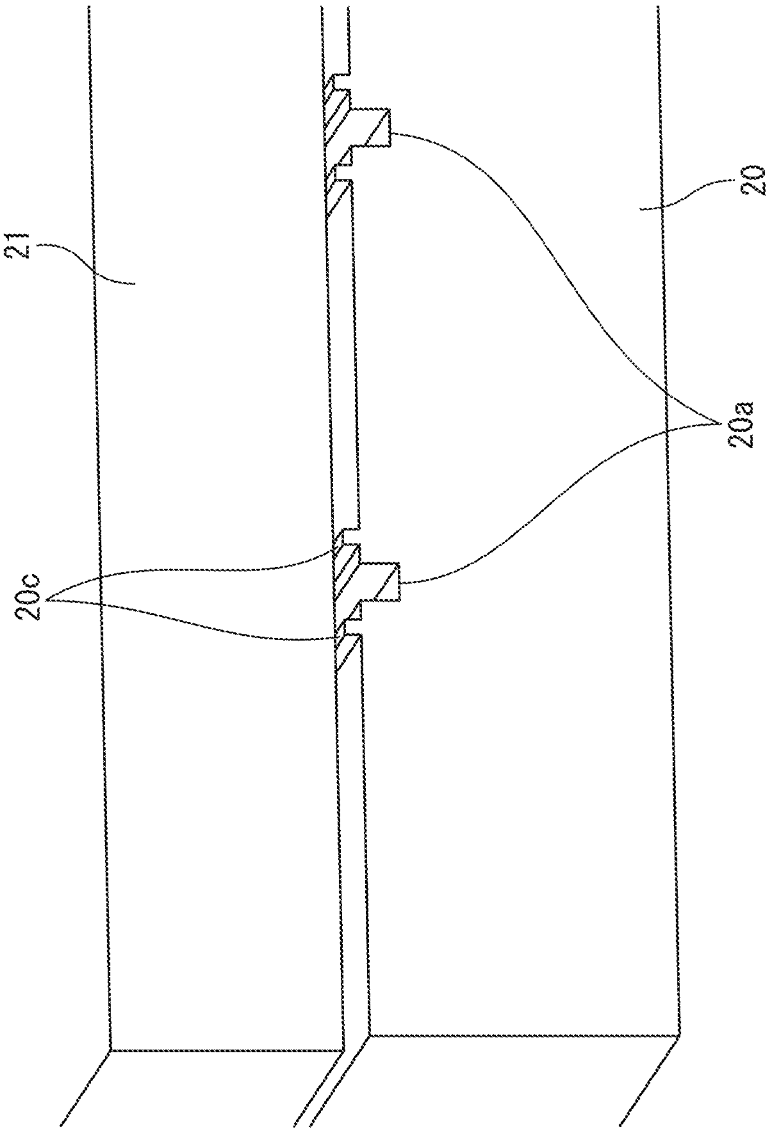
FIG. 3B is an enlarged sectional view of one example of a method of fixing a flat plate and a lid.

FIG. 3A and FIG. 3B illustrate one example of a method of fixing a flat plate and a lid. In order to shut off the fluid circuit 4 from the external space, banks 20*c* may be formed in advance on both sides of the groove 20*a* and the reservoir tank 20*b*, the flat plate 20 may be covered with the lid 21, and the groove 20*a* and the reservoir tank 20*b* may be sealed by heating the banks 20*c* by irradiating or applying laser light, ultrasonic waves, or the like to at least the banks 20*c* and welding the flat plate 20 and the lid 21. Alternatively, the lid 21 may be applied to the flat plate 20 including the groove 20*a* and the reservoir tank 20*b*, and at least the portions other than the groove 20*a* and the reservoir tank 20*b* may be heated by irradiating or applying laser light, ultrasonic waves, or the like, and the groove 20*a* and the reservoir tank 20*b* may be sealed by welding the flat plate 20 and the lid 21. In this case, all portions other than the groove 20*a* and the reservoir tank 20*b* are fixed, thus increasing the strength of the fixation.

Referring again to FIG. 1, the fluid circuit 4 includes at least an injection and discharge unit 10 and a cell induction and culture unit 13 as a plurality of functional sites. The fluid circuit 4 may optionally include a variable volume unit 11, a transfer unit 12, a fluid reservoir unit 14, a fluid mixing unit 15, a cell separation unit 16, and a cell mass disruption unit 17. Since these variety of functional sites are integrated in one cell production plate 2, manufacturing processes such as closed connection of separate parts via tubes, pumps, connectors, and the like are unnecessary, thereby reducing the man-hours and manufacturing cost of the cell production device 1.

The injection and discharge unit 10 includes an injection and discharge channel that injects or discharges fluid into or out of the fluid circuit 4 via the closed type connector 3. In order to enable a plurality of types of fluids to be injected or discharged, the injection and discharge unit 10 includes a plurality of injection and discharge channels 10*a*-10*f*. For example, the first injection and discharge channel 10*a* is capable of injecting or discharging fluids containing source cells and the like, while the second injection and discharge channel 10*b* is capable of injecting or discharging fluids such as reagents for source cell separation, anticoagulants, or phosphate-buffered saline. A third injection and discharge channel 10*c* is capable of injecting or discharging fluids such as inducing factor introduction reagents, and a fourth injection and discharge channel 10*d* is capable of injecting or discharging a variety of culture media such as initialization or induction medium, cell detachment reagents such as trypsin alternative recombinant enzymes, single cell separation reagents, or intercellular adhesion detachment agents. Examples of the culture medium for induction includes initialization medium, reprogramming medium, fate diversion medium, direct programming medium, differentiation diversion medium, differentiation induction medium, and transformation medium. Furthermore, a fifth injection and discharge channel 10*e* is capable of discharging or injecting fluid containing cells that have undergone at least one of induction and culture into the fluid container 19 as a sample, and a sixth injection and discharge channel 10*f* is capable of discharging or injecting fluid containing target cells into the fluid container. The fluid container 19 for sample discharge may be a closed type connector 3, such as a variable volume bag that connects to a heat-fused tube. When discharging a fluid containing target cells, a refrigerant such as liquid nitrogen may be supplied around the sixth injection and discharge channel 10*f* to freeze the fluid containing the target cells and seal the cell production plate, or the fluid container into which the fluid is discharged from the sixth injection and discharge channel 10*f* via the closed type connector 3 may be frozen with a refrigerant such as liquid nitrogen.

The variable volume unit 11 includes a physical or chemical variable volume material that stores a fluid that is extruded or withdrawn by injected or discharged fluid. A fluid relief flow path is provided to allow a fluid originally contained in the fluid circuit 4 to escape, and either a physical variable volume material is connected to the fluid relief flow path or a chemical variable volume material is placed in a reservoir tank with a pressure valve that opens and closes at a certain pressure in the fluid relief flow path, to allow fluid movement while keeping the fluid circuit 4 sealed. The physical variable volume material may be, for example, a flexible bag, or a syringe. The chemical variable volume material may include, for example, a fluid absorbent such as soda lime, or silica gel, and a fluid releaser that is placed in a different reservoir tank than the reservoir tank in which the fluid absorbent is placed. The variable volume material keeps the internal pressure of the closed fluid circuit 4 approximately constant, and the fluid extruded or withdrawn by the injected or discharged fluid is confined in the cell production plate 2. Therefore, there is no need to release fluid outside the cell production plate 2 or to take in fluid from outside, and the cell production plate 2 can be formed into a plate while maintaining airtightness of the fluid circuit 4. Such a cell production plate 2 is easy for a robot to handle.

The transfer unit 12 includes a pump that transfers a fluid in the fluid circuit 4. The pump can be a flow-controllable positive displacement pump, such as a rotary pump or a reciprocating pump. As the rotary pump, a peristaltic pump is preferred. In the case of a peristaltic pump, flexible tubing is hermetically connected to a connector at the end of the flow path, and fluid is transferred by squeezing the tubing with rollers. Since the tubing is blocked by the rollers, when the pump is stopped, the fluid flow is blocked and the flow rate can be controlled. As the reciprocating pump, a diaphragm pump is desirable. Note, however, that in the case of a diaphragm pump, since the diaphragm does not shut off the flow path, flow control is possible by using a flow shutoff valve in combination.

In order to transfer a fluid to an appropriate functional site at an appropriate time, the transfer unit 12 preferably includes a plurality of pumps P1-P8. For example, the first pump P1—the third pump P3 transfer a fluid stored in the fluid reservoir units A1-A3 at an appropriate timing, and the fourth pump P4 and the eighth pump P8 transfer the fluid stored in the cell separation unit 16 at an appropriate timing. The fifth pump P5 transfers a fluid stored in the fluid reservoir unit A4 at an appropriate timing, and the sixth pump P6—the seventh pump P7 transfer a fluid stored in the cell induction and culture unit 13 at an appropriate timing. When, for example, a peristaltic pump is used as a pump, a rotary encoder capable of detecting an amount of rotation may be provided on a rotation main shaft of the pump in order to obtain information on whether the pump is operating properly, such as whether the pump has reliably rotated or has rotated by an appropriate angle. Alternatively, for example, a visual mark may be provided at end of the rotation main shaft of the pump, and rotational movement of the mark may be captured directly in an image by an image recognition sensor. A flow measurement unit (not illustrated) may be further provided upstream or downstream of the pump to confirm that the pump is pumping reliably. The flow measurement unit may be, for example, a flow rate sensor provided adjacent to at least one of a flow path and a reservoir tank connected to a transfer unit, or an image recognition sensor that captures images of fluid changes over time in at least one of a flow path and a reservoir tank connected to the transfer unit. The flow rate sensor can employ a variety of measurement methods that do not adversely affect cells, such as the Kalman vortex type, impeller type, or diaphragm type, and directly obtains flow rate information of the fluid. The image recognition sensor obtains flow rate information from the movement of the fluid by image recognition from an external camera or the like via the transparent lid 21. The image recognition sensor may be diverted from other image recognition sensors herein, which reduces the number of parts and production cost.

The cell induction and culture unit 13 includes a cell induction and culture tank 13*a*, which performs at least one of cell induction and culture based on a transferred fluid, and a culture medium circulation path 13*b*, which is in fluid communication with the cell induction and culture tank 13*a* and circulates the culture medium. The cell induction and culture tank 13*a* is warmed to a predetermined culture temperature, for example 37° C., by a warming element. The culture medium circulation path 13*b* is cooled by a cooling element to a predetermined culture medium quality maintenance temperature, for example, 4° C.-8° C. The cell induction and culture tank 13*a* may be sealed and may not be supplied with fluids such as carbon dioxide, nitrogen, and oxygen, but at least one of the cell induction and culture tank 13*a* and the culture medium circulation path 13*b* may further include a fluid exchange filter that exchanges fluids such as carbon dioxide, nitrogen, and oxygen inside and outside the device. The cell induction and culture tank 13*a* may be a three-dimensional culture tank for cell suspension culture, or may be a two-dimensional culture tank for adhesion culture. For adhesion culture, the cell induction and culture tank 13*a* may be coated with a cell adhesion coating such as matrigel, collagen, polylysine, fibronectin, vitronectin, gelatin, and laminin, laminin fragments, or may be filled with hollow fibers. Furthermore, the cell induction and culture tank 13*a* may integrally include a culture tank 30 and a culture medium tank 31 that supplies culture medium to the culture tank 30. In this case, the cell induction and culture tank 13*a* preferably includes a specific component-permeable member 32, for example, a semipermeable membrane, which allows only specific components to pass between the culture tank 30 and the culture medium tank 31. The specific component-permeable member 32 permeates, for example, specific components such as a variety of culture media, coating agents for cell adhesion, and reagents for cell separation.

The cell induction and culture unit 13 may further include a pH measurement unit 13*c* for measuring the pH value of culture medium used. The pH measurement unit 13*c* is preferably provided in the culture medium circulation path 13*b* or the cell induction and culture tank 13*a* for measuring the pH value of culture medium used. The pH measurement unit 13*c* may be, for example, an image recognition sensor or an electrode measurement sensor. The image recognition sensor is used for hue measurement for pH values with an external camera or the like via a transparent lid. The electrode measurement sensor measures the pH value by the glass electrode method. In the case of hue measurement, at least a portion of the culture medium circulation path 13*b* (for example, the bottom of the hue measurement point) can be made white to allow accurate detection of the hue. This pH value makes it possible to quantitatively grasp the condition of the culture medium. In order to sharpen the contour of cell images on the image, the cell induction and culture tank 13*a* preferably further includes an illumination unit that illuminates the cell induction and culture tank 13*a* from at least one of the following directions: in front, in the surrounding direction (for example, perpendicular to the observation plane), and in the rear. The illumination unit includes, for example, LED illumination, and may be embedded inside the cell production plate 2, or may be provided outside the cell production plate 2 by making the cell induction and culture tank 13*a* more convex than the cell production plate 2. To allow illumination to reach cells, the culture tank 30 may be covered with a transparent material that allows light to pass through.

The fluid reservoir unit 14 includes a reservoir tank for storing a fluid to be injected into or discharged out of the fluid circuit 4. In order to enable storage of a plurality of types of fluids, the fluid reservoir unit 14 preferably includes a plurality of reservoir tanks A1-A4. The reservoir tanks A1-A4 are formed as locations where the width or depth of the flow path is relatively increased, enabling a variety of fluids to be utilized in predetermined amounts at appropriate timing. For example, the first reservoir tank A1 stores fluid containing source cells, the second reservoir tank A2 stores fluids such as reagents for cell separation, anticoagulants, and phosphate-buffered saline, the third reservoir tank A3 stores fluids such as reagents for inducing factors, and the fourth reservoir tank A4 stores fluids such as a variety of culture media, cell adhesion coating agents, and reagents for cell detachment. A reservoir tank for storing fluids containing target cells, or the like, may also be provided.

Figure 4A:
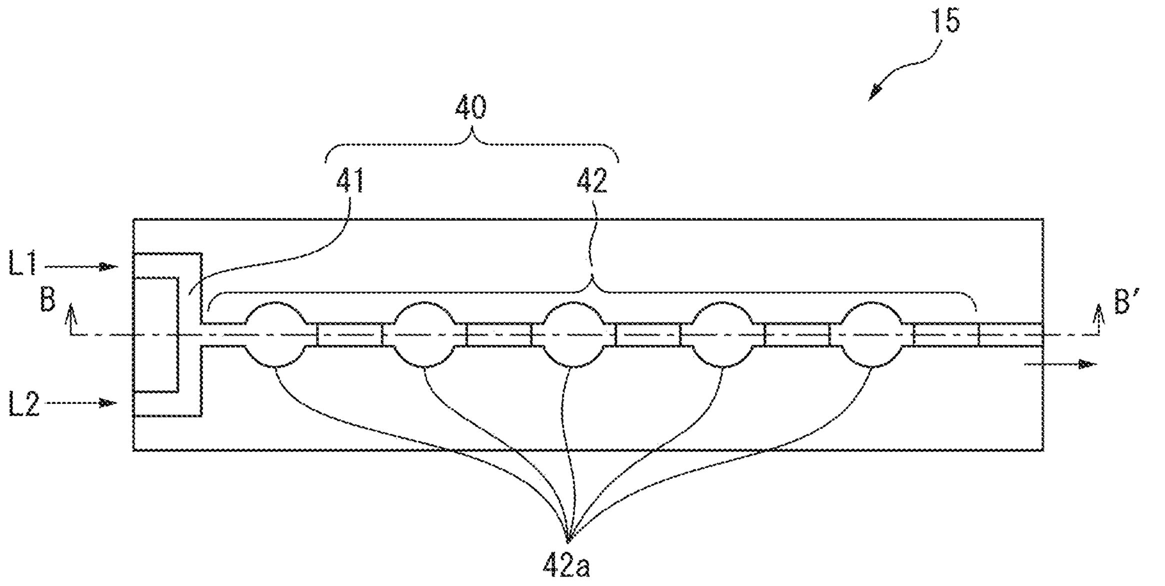
FIG. 4A is a plan view of one example of a mixing flow path.
Figure 4B:
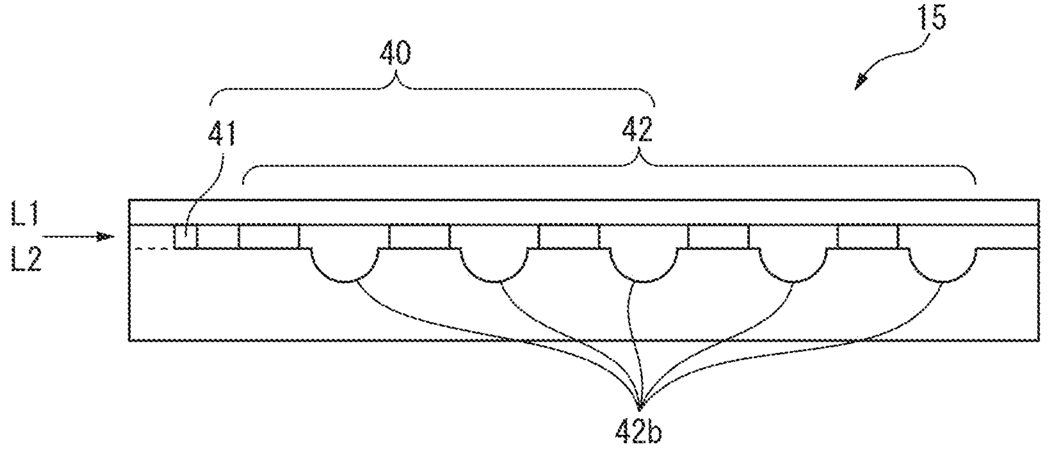
FIG. 4B is a B-B' sectional view illustrating one example of a mixing flow path.

The fluid mixing unit 15 includes a mixing flow path that mixes a plurality of mutually immiscible fluids. FIG. 4A and FIG. 4B illustrate one example of a mixing flow path. The mixing flow path 40 preferably includes a fluid merging path 41 and a mixed flow generation path 42. The fluid merging path 41 is a flow path that merges mutually immiscible fluids L1-L2 into a single flow path, and the mixed flow generation path 42 is a flow path that generates a mixed flow in the merged fluids L1-L2. The mixed flow generation path 42 is, for example, a flow path in which the cross-sectional area of the flow path is varied discontinuously, and it is preferable that at least one of a flow path width and a flow path depth is varied in a direction different from the direction of fluid flow. For example, the mixed flow generation path 42 alternately includes a flow path width change unit 42*a* and a flow path depth change unit 42*b* with respect to a direction of fluid flow. This makes it easier for mutually immiscible fluids L1-L2 to be mixed by alternately generating a mixed flow in which the flow is varied in the direction of the channel width and a mixed flow in which the flow is varied in the direction of the channel depth. As an alternative embodiment, the mixed flow generation path 42 may be a spiral flow path that passes from a front side to a back side of the flat plate. In order to return the fluid from the back side of the flat plate to the front side, two spiral flow paths penetrating the flat plate are provided, and a communication path in fluid communication between these spiral flow paths is provided on the back side of the flat plate.

Referring again to FIG. 1, the cell separation unit 16 includes separation tanks D1-D2 for separating cells or cell masses. For example, the separation tanks D1-D2 are reservoir tanks formed by relatively increasing the width or depth of the flow paths, and the first separation tank D1 separates fluid containing only source cells from fluid containing source cells, and the second separation tank D2 allows only relatively large cell masses to settle and separate from the rest of the cell masses. As a method of separating the source cells, reagents for source cell separation, panning, magnetic cell separation (MACS), flow cytometry, or the like can be used.

Figure 5:
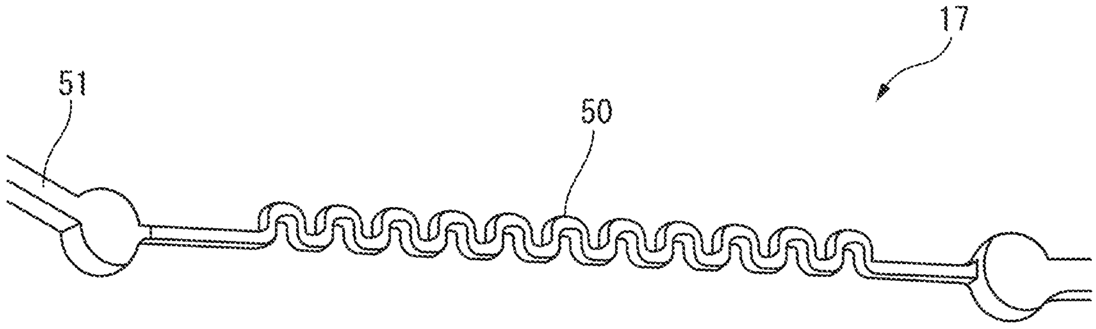
FIG. 5 is an enlarged perspective view of one example of a disruption flow path.

The cell mass disruption unit 17 includes a disruption flow path that further disrupts separated cell masses (mass of one or more cells). FIG. 5 illustrates one example of a disruption flow path. The disruption flow path 50 has a relatively small flow path area compared to the upstream flow path 51, and is preferably meandering. By meandering the flow path, a latent flow is generated, which applies shearing stress to the cell mass and breaks up a large growing cell mass into smaller cell masses. Latent flow is, for example, any of the following: flow that produces whirlpools, turbulence, reverse flow, flow that produces portions with different flow speeds, flow that produces shearing forces, and flow that produces portions where flows with different directions of travel collide.

Figure 6:
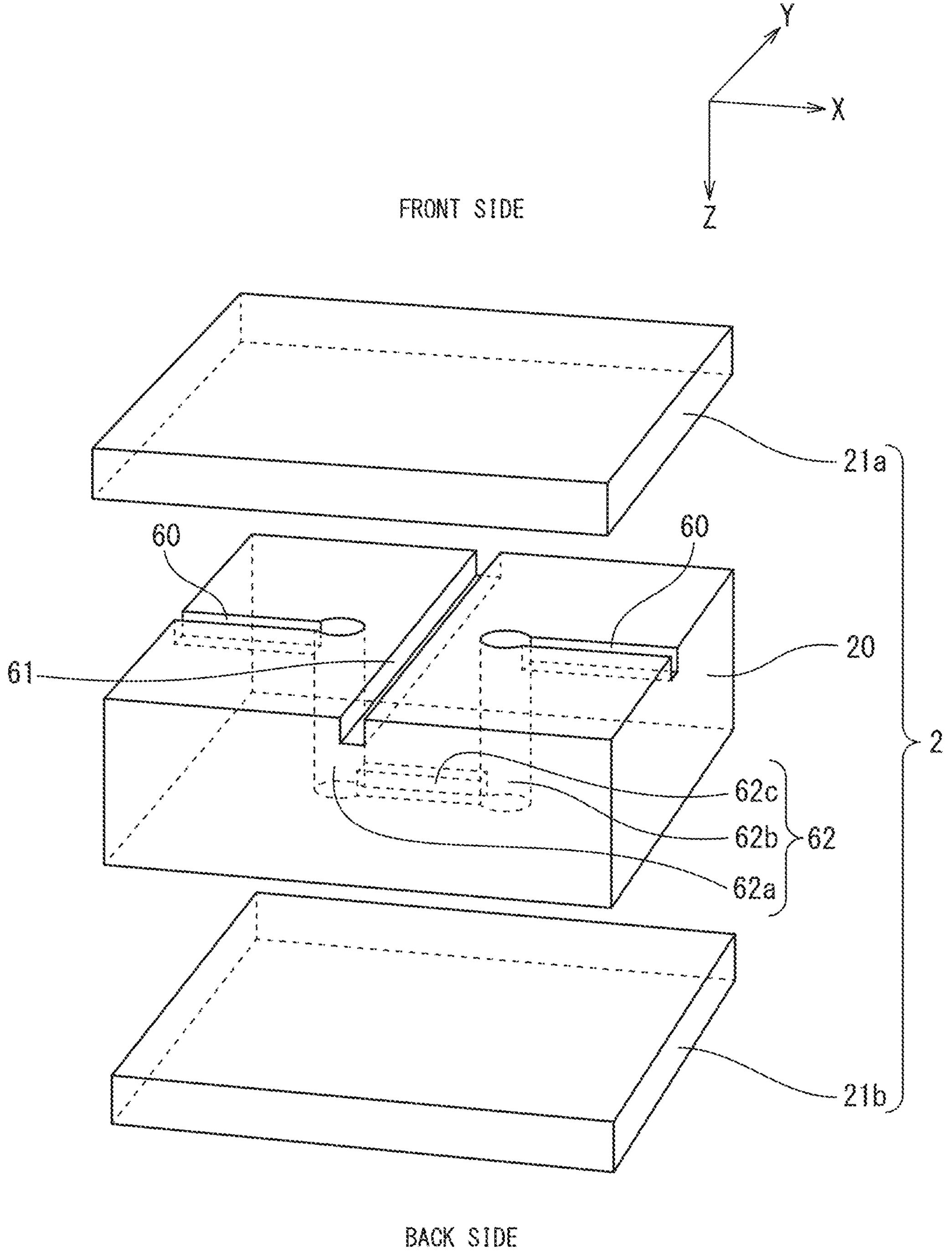
FIG. 6 is an enlarged perspective view of one example of a cross flow path.

Since a plurality of functional sites as described above are integrated into a fluid circuit 4 in one cell production plate 2, the fluid circuit 4 includes cross flow paths that extend in a variety of directions and cross in complex ways. FIG. 6 illustrates one example of a cross flow path. The cross flow path includes a first flow path 60 extending in the X direction and a second flow path 61 extending in the Y direction, which is different from the X direction, on a front side of the cell production plate 2, and the first flow path 60 includes a detour path 62 extending toward a back side of the cell production plate 2 and detouring the second flow path 61. For example, the detour path 62 preferably includes two through holes 62*a*-62*b* that penetrate from the front side to the back side of the flat plate 20, and a communication path 62*c* that communicates between the through holes 62*a*-62*b* at the back side of the flat plate 20. In order to cover the communication path 62*c* formed on the back side of the flat plate 20, the lid 21 desirably includes a front lid 21*a* that covers the front side of the flat plate 20 and a back lid 21*b* that covers the back side of the flat plate 20. Such a cross flow path can provide a small cell production plate 2 that includes a highly integrated fluid circuit 4.

Figure 7A:
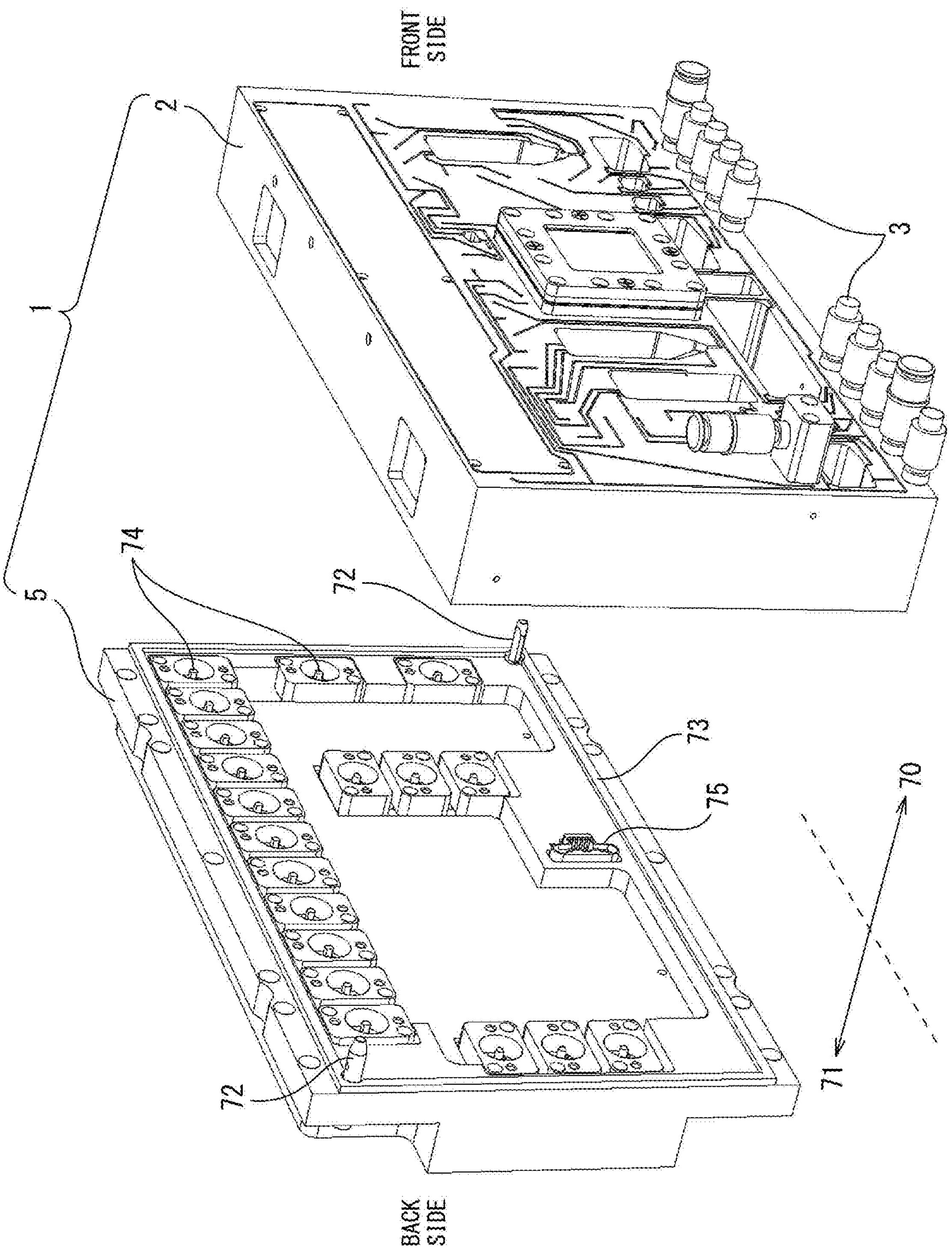
FIG. 7A is a frontal perspective view of one example of a base plate.
Figure 7B:
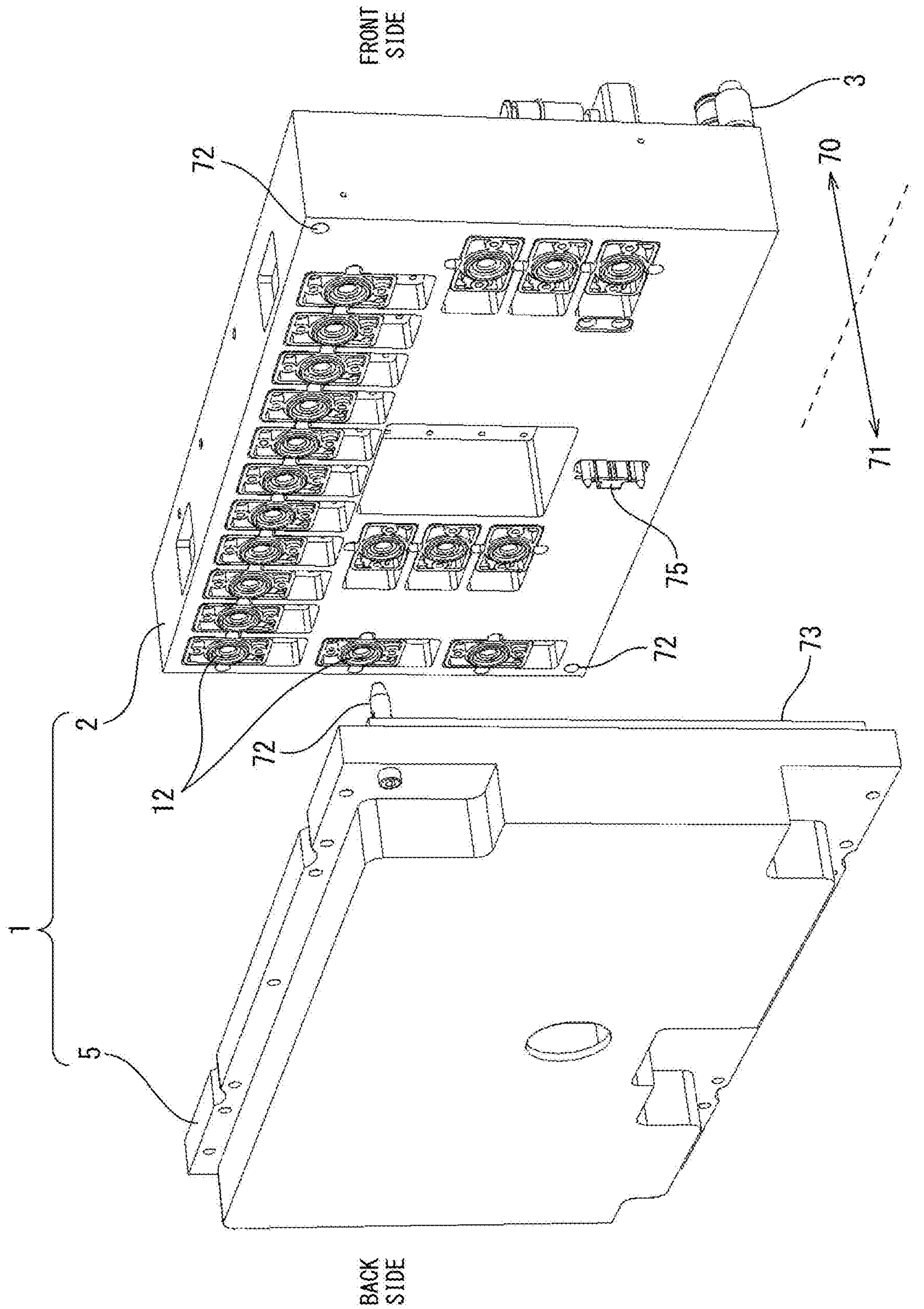
FIG. 7B is a back perspective view of one example of a base plate.

The cell production device 1 preferably further includes a base plate that is removably connected to the cell production plate 2. FIG. 7A and FIG. 7B illustrate one example of the base plate. The base plate 5 provides fluid control, temperature control, and the like for the cell production plate 2. The cell production plate 2 is arranged to face a dangerous area side 70 where robots and the like act, whereas the base plate 5 is arranged to face a safe area side 71 opposite to the dangerous area side 70. From the viewpoint of preventing biological contamination, the cell production plate 2 may be disposable and the base plate 5 may be reusable. The cell production device 1 is configured to be maintainable from the safety area side 71. When the cell production device 1 has such a two-sided structure, robots and the like can engage with a plurality of cell production devices 1 on a one-to-many basis.

The cell production device 1 may further include a positioning member 72 and a plate sealing member 73 on connecting surfaces of the cell production plate 2 and the base plate 5. The positioning member 72 may be a convex portion and a concave portion that fit each other, and positions the connection position of the cell production plate 2 and the base plate 5. The plate sealing member 73 may be a gasket, packing, or the like attached to the outer circumference of the connecting surface, and by connecting the cell production plate 2 and the base plate 5, the inside of the plate sealing member 73 is shut off from the external space and gas permeation from the back side of the cell production plate 2 is inhibited. The base plate 5 includes a drive unit 74 that drives the transfer unit 12. The drive unit 74 includes a motor that drives a peristaltic pump, for example. Furthermore, the connecting surface of the cell production plate 2 and the base plate 5 preferably includes electrical contacts 75 that supply power to electrical elements to be placed on the cell production plate 2, such as warming elements, cooling elements, flow sensors, and the like.

According to the above-described embodiment, since a plurality of functional sites are integrated in one cell production plate 2, the time and effort required to connect separate components via tubes, pumps, connectors, and the like in a closed manner is eliminated, and production of the cell production device 1 is streamlined. At the same time, the fluid extruded or withdrawn by the injected or discharged fluid is confined in the cell production plate 2. Therefore, there is no need to release fluid outside the cell production plate 2 or to take in fluid from outside, and the cell production plate 2 can be formed into a plate while maintaining sealability of the fluid circuit 4. Such a plate-shaped cell production plate 2 is easy for a robot to handle, which improves compatibility with automated systems.

Although various embodiments have been described herein, it is to be recognized that the present invention is not limited to the various embodiments described above, and that various changes can be made within the scope of the following claims.

REFERENCE SIGNS LIST

1 Cell production device
2 Cell production plate
3 Closed type connector
4 Fluid circuit
5 Base plate
10 Injection and discharge unit
10*a*-10*f* First-sixth injection and discharge channel
11 Variable volume unit
12 Transfer unit
13 Cell induction and culture unit
13*a* Cell induction and culture tank
13*b* Culture medium circulation path
13*c* pH measurement unit
14 Fluid reservoir unit
15 Fluid mixing unit
16 Cell separation unit
17 Cell mass disruption unit
19 Fluid container
20 Flat plate
20*a* Groove
20*b* Reservoir tank
20*c* Bank
21 Lid
21*a* Front lid
21*b* Back lid
30 Culture tank
31 Culture medium tank
32 Specific component-permeable member
40 Mixing flow path
41 Fluid merging path
42 Mixed flow generation path
42*a* Flow path width change unit
42*b* Flow path depth change unit
50 Disruption flow path
51 Upstream flow path
60 First flow path
61 Second flow path
62 Detour path
62*a*-62*b* Through hole
62*c* Communication path
70 Dangerous area side
71 Safe area side
72 Positioning member
73 Plate sealing member
74 Drive unit
75 Electrical contact
A1-A4 First-fourth reservoir tank
D1-D2 First-second separation tank
L1-L2 First-second fluid
P1-P8 First-eighth pump
S External space

The invention claimed is:

1. A cell production device, comprising:

a cell production plate that includes a fluid circuit in which a plurality of functional sites are integrated; and a closed connector that connects the fluid circuit to an external space in a closed manner, wherein the fluid circuit comprises, as the plurality of functional sites, an injection and discharge unit configured to inject or discharge a fluid into or out of the fluid circuit via the closed connector, a cell induction and culture unit configured to perform induction and culture of cells based on the injected fluid, and a fluid mixing unit configured to mix a plurality of mutually immiscible fluids, wherein the fluid mixing unit includes a fluid merging path configured to merge the plurality of mutually immiscible fluids into a single flow path, wherein the fluid mixing unit includes a mixed flow generation path configured to generate a mixed flow in the fluids merged in the fluid merging path, wherein the mixed flow generation path alternately includes a flow path wider part, which expands a flow path width in one direction different from a direction of fluid flow, and a flow path deeper part, which increases a flow path depth in another direction different from the one direction and the direction of fluid flow, with respect to the direction of fluid flow, and wherein the flow path wider part and the flow path deeper part are each constituted by a curved surface.

2. The cell production device according to claim 1, further comprising a variable volume unit configured to store a fluid that is extruded or withdrawn by the injected or discharged fluid, wherein the variable volume unit comprises a physical or chemical variable volume material.

3. The cell production device according to claim 2, wherein the physical variable volume material is a flexible bag or a syringe.

4. The cell production device according to claim 1, wherein the fluid circuit further comprises a transfer unit configured to transfer the injected fluid within the fluid circuit.

5. The cell production device according to claim 4, wherein the fluid circuit further comprises a flow measurement unit upstream or downstream of the transfer unit.

6. The cell production device according to claim 5, wherein the flow measurement unit comprises a flow rate sensor provided adjacent to at least one of a flow path or a reservoir tank communicating with the transfer unit.

7. The cell production device according to claim 5, wherein the flow measurement unit comprises an image recognition sensor configured to capture images of fluid succession changes in at least one of a flow path or a reservoir tank communicating with the transfer unit.

8. The cell production device according to claim 1, wherein the injection and discharge unit comprises an injection and discharge channel configured to discharge or inject fluid containing the cells subjected to at least one of the induction or the culture as a sample outside the fluid circuit or into the fluid circuit.

9. The cell production device according to claim 1, wherein the fluid circuit further comprises a cell separation unit configured to separate cells or cell masses.

10. The cell production device according to claim 1, wherein at least a portion of the cell production plate is transparent.

11. The cell production device according to claim 1, wherein the fluid circuit comprises a first flow path extending in a first direction and a second flow path extending in a second direction different from the first direction on a front side of the cell production plate, and the first flow path comprises a detour path that extends toward a back side of the cell production plate and detours the second flow path.

12. The cell production device according to claim 11, wherein the cell production plate comprises a flat plate and a lid covering the flat plate, and the detour path comprises a plurality of through holes penetrating from the front side to the back side of the flat plate, and a communication path communicating between the through holes at the back side of the flat plate.

13. The cell production device according to claim 1, further comprising a base plate detachably connected to the cell production plate, and a plate sealing member attached to connecting sides of the cell production plate and the base plate.

14. The cell production device according to claim 1, comprising a base plate that is detachably connected to the cell production plate, wherein the fluid circuit comprises a peristaltic pump configured to transfer the injected fluid in the fluid circuit, and the base plate comprises a drive unit configured to drive the peristaltic pump.

15. The cell production device according to claim 14, further comprising an image recognition sensor configured to capture a state of rotational movement of the peristaltic pump in an image.

16. A method of producing a cell production device, the method comprising:

forming a flat plate that includes a fluid circuit in which a plurality of functional sites are integrated;

forming a cell production plate by fixing a lid to the flat plate in such a manner to cover the fluid circuit; and attaching a closed connector to the cell production plate to connect the fluid circuit to an external space in a closed manner, wherein the fluid circuit comprises, as a plurality of functional sites, an injection and discharge unit configured to inject or discharge a fluid into or out of the fluid circuit via the closed connector; and a cell induction and culture unit configured to perform induction and culture of cells based on the injected fluid, and a fluid mixing unit configured to mix a plurality of mutually immiscible fluids, wherein the fluid mixing unit includes a fluid merging path configured to merge the plurality of mutually immiscible fluids into a single flow path, wherein the fluid mixing unit includes a mixed flow generation path configured to generate a mixed flow in the fluids merged in the fluid merging path, wherein the mixed flow generation path alternately includes a flow path wider part, which expands a flow path width in one direction different from a direction of fluid flow, and a flow path deeper part, which increases a flow path depth in another direction different from the one direction and the direction of fluid flow, with respect to the direction of fluid flow, and wherein the flow path wider part and the flow path deeper part are each constituted by a curved surface.

17. The method according to claim 16, wherein the forming the flat plate comprises forming a groove or a reservoir tank as the fluid circuit on at least one of a front side or a back side of the flat plate.

* * * * *